US008758837B2

(12) United States Patent
Liu et al.

(10) Patent No.: US 8,758,837 B2
(45) Date of Patent: Jun. 24, 2014

(54) METHOD FOR REMOVING PESTS FROM HARVESTED VEGETABLES

(75) Inventors: Tin-Yin Liu, Hsinchu (TW); Yi-Kai Wang, Hsinchu (TW); Mei-Ling Lu, Hsinchu (TW)

(73) Assignee: Food Industry Research & Development Institute (TW)

( * ) Notice: Subject to any disclaimer, the term of this patent is extended or adjusted under 35 U.S.C. 154(b) by 795 days.

(21) Appl. No.: 12/458,203

(22) Filed: Jul. 2, 2009

(65) Prior Publication Data

US 2009/0311352 A1 Dec. 17, 2009

Related U.S. Application Data

(63) Continuation-in-part of application No. 11/819,593, filed on Jun. 28, 2007, now abandoned.

(51) Int. Cl.
*A61K 36/00* (2006.01)
*A61K 36/31* (2006.01)

(52) U.S. Cl.
USPC ........... 424/755; 424/773; 424/725; 424/777; 424/778; 424/779; 424/774

(58) Field of Classification Search
None
See application file for complete search history.

(56) References Cited

U.S. PATENT DOCUMENTS

| 5,113,881 | A | * | 5/1992 | Lin et al. ............................ 134/1 |
| 5,821,376 | A | | 10/1998 | Rathfelder et al. |
| 6,207,705 | B1 | * | 3/2001 | Coats et al. .................... 514/514 |
| 2003/0091518 | A1 | * | 5/2003 | Pauly et al. ..................... 424/59 |
| 2004/0266621 | A1 | | 12/2004 | West |
| 2006/0064925 | A1 | | 3/2006 | Morgan |

FOREIGN PATENT DOCUMENTS

EP 1985182 A3 10/2008
WO WO 2006/085768 A2 8/2006

OTHER PUBLICATIONS

Stewart, Quarter-plant samples to detect populations of *Lepidoptera noctuidae* Pieridae and Plutellidae on cauliflower, Journal of Economic Entomology, (1989) vol. 82, No. 3, pp. 829-883.*
Narang et al, Effect of leaf extracts containing glucosinolates on the biology of mustard aphid, *Lipaphis erysimi* (Kalt.), Indian J. Ecol., 13 (2) : 307-312 (1986).*

Charron et al, Inhibition of *Pythium ultimum* and *Rhizoctonia solani* by shredded leaves of *Brassica* species, J. Amer. Soc. Hort. Sci. 124 (5): 462-467, 1999.*
Siemens et al, Glucosinolates and herbivory by specialists (*Coleoptera: chrysomelidae, Lepidoptera: plutellidae*): consequences of concentration and induced resistance, Environmental entomology, Dec. 1996. vol. 25, No. 6. p. 1344-1353.*
Sharma et al., "Use of Plant Extract and yeast antagonists in the management of storage scab and rots of apple fruits" J. Biol. Control, 14(1): 17-23, 2000.
Hou et al., "Chintinase activity of sweet potato (*Ipomoea batatas* [L.] Lam. var. Tainong 57)" Bot. Bull. Acad. Sin 39:93-97, 1998.
Narang et al., "Effect of Leaf Extracts Containing Glucosinolates on the Biology of Mustard Aphid, *Lapaphis erysimi* (Kalt.)" Indian J. Ecol., 13(2): 307-312, 1986.
Charron et al., "Inhibition of *Pythium ultmum* and *Rhizoctonia solani* by Shredded leaves of *Brassica* Species", J. Amer. Soc. Hort. Sci., 124(5):462-467, 1999.
Selijasen et al. "Effects of Neem on Oviposition and Egg and Larval Development of *Mamestra brassicae* L: Dose Response, Residual Activity, Repellent Effects and System Activity in Cabbage Plants" Elsevier Science, GB, 25(4): 338-345, 2006.
Shukla Abhishek et al., "Evaluation of Some Plant Extracts as Repellents Against Shoot and Fruit Borer, Earias Vittella Fab. in Okra Crop", Geobios, University of Jodhpur, Jodhpr, IN, 24(I): 35-39, 1997.
Khan A. et al., Tropical Agriculture, 80(1): 19-21, 2003.
Nascimento de Vasconcelos Geraldo Jose et al., Ciencia Rural, 36(5): 1353-1359. 2006.
Manfre Medeiros Cesar Augusto et al., Braganitia 64(4): 633-641, 2005.
Kianmatee Supawan et al., Journal of Asian—Pacific Entomology 10(1): 69-74, 2007.
English transcript of abstract JP 2001 158711A.
Srinivasan R. et al., Current Science, 90(6): 846-850, 2006.

* cited by examiner

*Primary Examiner* — Qiuwen Mi
(74) *Attorney, Agent, or Firm* — Andrews Kurth LLP; Aldo Noto; Michael Ye

(57) ABSTRACT

A method for removing pests from harvested vegetables has steps of extracting a first portion of harvested vegetables to obtain a vegetable cleanser, and cleaning a second portion of harvested vegetables with the vegetable cleanser, such that pests residing on the second portion of harvested vegetables are removed from the second portion of harvested vegetables, wherein the first portion of harvested vegetables and the second portion of harvested vegetables independently contain vegetables selected from the group consisting of vegetables belonging to the families of Cruciferae, Compositae, Chenopodiaceae and Amaranthaceae. The aforementioned method is effective at removing pests from harvested vegetables and satisfies urgent needs to reduce use of chemical pesticides.

16 Claims, 1 Drawing Sheet

US 8,758,837 B2

METHOD FOR REMOVING PESTS FROM HARVESTED VEGETABLES

RELATED APPLICATION

The present invention is a Continuation-in-Part (CIP) of U.S. patent application Ser. No. 11/819,593 filed on Jun. 28, 2007, now abandoned which is incorporated by reference in the present application in its entirety.

BACKGROUND OF THE INVENTION

Field of the Invention

The present invention relates to methods for removing pests from harvested vegetables, particularly to methods for removing pests from harvested vegetables belonging to the families of Cruciferae, Compositae, Chenopodiaceae and Amaranthaceae.

SUMMARY OF THE INVENTION

An important objective of the present invention is to provide methods for efficiently removing pests from harvested vegetables by a nontoxic and natural vegetable cleanser that displays no harmful effects as known in artificial cleansers.

To achieve the objective, the present invention provides a method for removing pests from harvested vegetables, comprising:

extracting a first portion of harvested vegetables to obtain a vegetable cleanser, and cleaning a second portion of harvested vegetables with the vegetable cleanser, such that pests residing on the second portion of harvested vegetables are removed from the second portion of harvested vegetables, wherein the first portion of harvested vegetables and the second portion of harvested vegetables independently contain vegetables selected from the group consisting of vegetables belonging to the families of Cruciferae, Compositae, Chenopodiaceae and Amaranthaceae.

Also disclosed is a method for removing pests from a vegetable, comprising:

washing a first vegetable with a cleanser extracted from a second vegetable, wherein the first vegetable and the second vegetable are selected from the group consisting of vegetables belonging to the families of Cruciferae, Compositae, Chenopodiaceae and Amaranthaceae.

The second vegetable can be the same as, or different from, the first vegetable. The second vegetable can also be an impalatable part of the first vegetable. The cleanser can be extracted by homogenizing the second vegetable and filtering the homogenate to remove debris.

Other objectives, advantages and novel features of the invention will become more apparent from the following detailed description when taken in conjunction with the accompanying drawings.

DETAILED DESCRIPTION OF THE INVENTION

Figure 1:
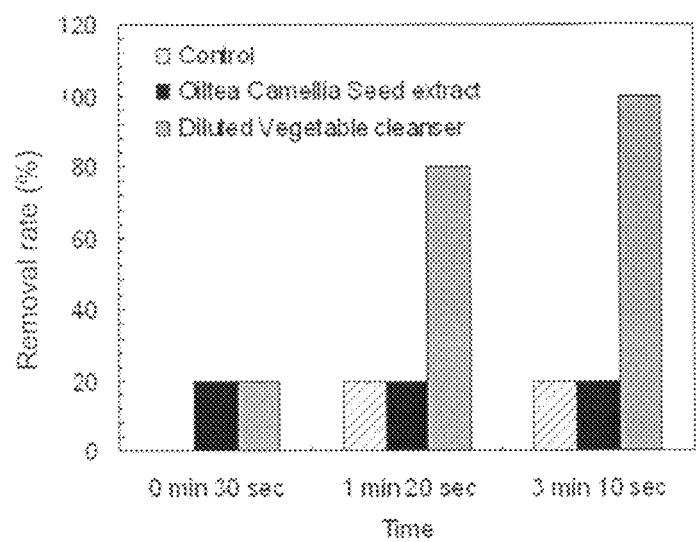
FIG. 1 illustrates removal rates of different treatments for removing pests from harvested vegetables according to Table 2.

There is a need to eliminate pests from harvested vegetables by nontoxic and natural cleanser. Vegetables cleaned with nontoxic and natural cleanser are desirable in markets, especially in ready-to-eat or ready-to-cook vegetable markets.

The present invention is based on introducing competitive vegetable extracts to vegetables with pests attached. Upon contact with the vegetable extracts, the attached pests relax and release from the vegetables.

The present invention provides an effective method for removing pests from harvested vegetables and satisfies urgent needs for reducing use of chemical cleansers. Furthermore, the method in accordance with the present invention can be applied to various agricultural products, not limited to certain species of vegetables.

A method for removing pests from harvested vegetables in accordance with the present invention comprises steps of:

extracting a first portion of harvested vegetables to obtain a vegetable cleanser, and cleaning a second portion of harvested vegetables with vegetable cleanser, such that pests residing on the second portion of harvested vegetables are removed from the second portion of harvested vegetables, wherein the first portion of harvested vegetables and the second portion of harvested vegetables independently contain vegetables selected from the group consisting of harvested vegetables belonging to the families of Cruciferae (also known as Brassicaceae), Compositae, Chenopodiaceae and Amaranthaceae.

The term "vegetable" as used herein refers to agricultural plants.

According to the present invention, the vegetables are selected from the group consisting of vegetables belonging to the families of Cruciferae, Compositae, Chenopodiaceae and Amaranthaceae.

Preferably, the vegetables are selected from the group consisting of vegetables belonging to genuses of *Brassica, Raphanus, Lactuca, Spinacia,* and *Amaranthus.*

More preferably, the vegetables are selected from the group consisting of *Brassica oleracea* (cauliflower), *Brassica oleracea* L. (cabbage), *Brassica oleracea* var. *italica* (broccoli), *Brassica napus* (canola), *Brassica rapa* perkinensis (Chinese cabbage), *Brassica juncea* (seedy mustard), *Raphanus sativus* (radish celery), *Lactuca sativa* Linn (lettuce), *Spinacia oleracea* L. (spinach) and *Amaranthus tricolor* L. (edible amaranth).

The term "vegetable cleanser" as used herein refers to a substance or composition obtained from a whole plant or parts of plant. Chemical and/or physical action, as would be understood in the art, may be required to obtain the substance or composition from whole plant or parts of plant. In a preferred embodiment, extracting the collected portion of the first vegetable comprises extracting the collected portion of the first vegetable with an aqueous solution, such as water, saline solution or the like.

The term "pest" or "worm" as used herein refers to organisms that cause illness, damage or consume food materials, such as crops or vegetables.

According to the present invention, pests include, but are not limited to, diamondback moth (*Plutella xylostella*); small white butterfly (*Pieris rapae* crucivora Boisduval); Cabbage looper [*Trichoplusia ni* (Hubner)]; aphids such as turnip aphid [*Lipaphis erysimi* (Kaltenbach)], green peach aphid [*Myzus persicae* (Sulzer)], and cabbage aphid [*Brevicoryne brassicae* (L.)]); harlequin bug [*Murgantia histrionica* (Hahn)]; beet armyworm [*Spodoptera exigua* (Hubner)]; cabbage webworm [*Hellula rogatalis* (Hulst)]; cutworms such as black cutworm [*Agrotis ipsilon* (Rott.)] and granulate cutworm [*Feltia subterranea* (Fabricius)]; yellow margined leaf beetle (*Microtheca ochroloma* Stal) and cross-striped cabbageworm [*Evergestis rimosalis* (Guenée)].

The diamondback moth is a serious pest for cruciferae plants, such as lettuce, spinach and amaranth. The female moth attaches her eggs to the lower leaf surface, either singly or in groups of two or three. Within a few days, the eggs hatch, and the larvae begin to feed on the underside of the leaf. Larvae of the diamondback moth, if disturbed will drop from the leaf suspended by a strand of silk so are not easily removed. Therefore, larvae of diamondback moth are used as sample pests in the following examples.

According to the present invention, pests include, but are not limited to organisms belonging to families of Plutellidae and Pieridae. Preferably, the pests in accordance with the present invention are selected from the group consisting of organisms belonging to genuses of *Plutella* and *Pieris*. More preferably, the pests in accordance with the present invention are selected from the group consisting of *Plutella xylostella* and *Pieris rapae* crucivora Boisduval.

In a preferred embodiment of the method in accordance with the present invention, the first portion of harvested vegetables and the second portion of harvested vegetables are independently selected from the group consisting of *Brassica oleracea* and *Brassica oleracea* var. italica; and more preferably, the pests are larvae of *Plutella xylostella* or *Pieris rapae* crucivora Boisduval.

In a preferred embodiment of the method in accordance with the present invention, extracting the first portion of harvested vegetables includes homogenizing the first portion of harvested vegetables to obtain a liquid composition as the vegetable cleanser.

According to the present invention, the term "homogenizing" includes any processes to make uniform in consistency, such as, but not be limited to, cutting, grinding and the like.

According to the present invention, the method as described above further comprises a step of collecting impalatable parts of harvested vegetables to provide the first portion of harvested vegetables and to leave uncollected parts of the vegetables as the second portion of harvested vegetables.

According to the present invention, the uncollected parts of the vegetables are edible parts of harvested vegetables.

According to the present invention, the term "impalatable parts" as used herein refers to parts of plants that are not usually used as food for human, such as roots, old or damaged leaves or stems of vegetables.

The term "impalatable parts" include, but are not limited to, roots, stems, leaves, flowers and fruits, which depend on the genera of the vegetables. For instance, cauliflower, which is a while stalk, or flower head, surrounded by green leaves, is one of several vegetables of the species *Brassica oleracea*, in the family Brassicaceae. In general, only the flower head of cauliflower is eaten, while the green leaves are considered as impalatable parts and usually discarded. More particularly, for cabbage and lettuce, two outside lamellae of leaves, yellow (brown) leaves, stems and brown inner leaves are impalatable; for cauliflower and broccoli, outside leaves, bolting and mature outside leaves or stems are impalatable; for canola, celery, spinach and seedy mustard, the region between stems and roots, mature organs or yellow leaves are impalatable; and for radish, leaves, stems and rootstalk skin are impalatable.

According to the present invention, the method as described above further comprises steps of filtering the vegetable cleanser to obtain a filtered vegetable cleanser and cleaning the second portion of harvested vegetables with the filtered vegetable cleanser.

In a preferred example of the present invention, the method as described above further comprises steps of: diluting the filtered vegetable cleanser to obtain a diluted vegetable cleanser and cleaning the second portion of harvested vegetables with the diluted vegetable cleanser.

In a preferred example of the present invention, the step of diluting of the filtered vegetable cleanser in the method as described above comprises: diluting the filtered vegetable cleanser at about a ratio of 1:50 by volume.

In a preferred example of the method in accordance with the present invention, the step of cleaning of the second portion of harvested vegetables includes soaking, washing or stirring the second portion of harvested vegetables in the vegetable cleanser.

In a preferred example of the method in accordance with the present invention, the step of cleaning the second portion of harvested vegetables includes stirring the second portion of harvested vegetables in the vegetable cleanser at a stirring rate ranging from about 50 to 110 rpm, and preferably, from 100 to 110 rpm The following examples are intended to assist the reader in practicing the invention and are not intended to be limiting in any way.

EXAMPLES

Materials and methods

Fresh broccoli and cauliflower harvested on rainy days were purchased from a local market. Plants of broccoli (*Brassica oleracea* var. italica) and cauliflower (*Brassica oleracea*) were randomly selected and used as sample vegetables in the following examples. Number of worms on each plant of the broccoli or cauliflower was counted. Fully randomized designs were used with three replicates in each experiment. As shown in Table 1, there were a few pests including diamondback moth (*Plutella xylostella*) and small white butterfly (*Pieris rapae* crucivora Boisduval) residing on the harvested broccoli and cauliflower as expected.

TABLE 1

Number of worms on each individual plant of broccoli and cauliflower

| Species | Number of worms on each plant* |
|---|---|
| Cauliflower | 55 |
| Broccoli | 9 |

*Data are presented as mean value of three individual experiments

Applicants found amounts of pests residing on cruciferae vegetables, such as broccoli and cauliflower, vary with weather conditions (such as sunny, cloudy or rainy) when the cruciferae vegetables are harvested. Thus showing that numbers of pests on each plant of cruciferae vegetables increases on the rainy days compared to other weather. Particularly, the amount of pesticide used on vegetables might be significantly increased on rainy days by cultivators. To further examine and evaluate the effect of vegetable cleanser in accordance with the present invention, broccoli and cauliflower were used as sample vegetables in the following examples.

Example 1

Evaluation of Effectiveness of Vegetable Cleanser Obtained from Cauliflower or Broccoli on Removing Pests from their Corresponding Host Vegetables 1.1 Preparation of Vegetable Cleanser, *Oiltea Camellia* Seed Extract and Vegetables where a Determined Number of Worms were Disposed in Advance 50 g of old and damaged leaves or stems of cauliflower and broccoli were individually homogenized in 500 ml water at 1000 to 2000 rpm for 2 minutes or more by homogenizer and then filtered to remove residue to obtain a filtered vegetable cleanser.

*Oiltea camellia* seed extract was obtained by diluting a commercial *Oiltea camellia* seed extract stock with water at a ratio of 1:200 by volume and used as control in the following experiments.

5 or 10 worms, larva of *Plutella xylostella* (Linnaeus 1758), were disposed on each plant of sample vegetables and allowed to adapt to sample vegetables to reduce stress caused by changing environment, wherein applicants had ascertained that Larva of *Plutella xylostella* grabbed sample vegetables to a certain extent that reduced eradication by hydrodynamic force. Obtained plants of sample vegetables harboring worms were used in the following experiments for mimicking normal parasitism of normally cultivated vegetables.

1.2 Process for Removing Pests from Harvested Vegetables

An appropriate amount of vegetable cleanser was diluted in a beaker with 2 liters of water at a ratio of vegetable cleanser to water of 1:50. A plant of sample vegetable was put into and soaked, washed or stirred in diluted vegetable cleanser, *Oiltea camellia* seed extract or water to remove pests therefrom. Hereby, *Oiltea camellia* seed extract and water were used as control. As stirring was conducted, stirring rates were set at 50 to 110 rpm. Optimal stirring rate would be 105 rpm. For confirming accuracy of estimated removal rate, experiments were conducted with sample vegetable harboring various numbers of worms (5 or 10 worms) as described above.

After the sample vegetables were subject to diluted vegetable cleanser, number of floating or sunk pests was counted. The removal rate of the vegetable cleanser to pest was calculated as a ratio of the number of floating or sunk pests to that of pests originally resided on the vegetable, which was five or ten for each plant of harvested vegetables.

1.3 Results

The number of worms removed by various treatments were shown in Table 2 and the removal rates of different treatments were calculated according to data of Table 2. As shown in Table 2 and FIG. 1, removal rate of the vegetable cleansers in accordance with the present invention was largely greater than *Oiltea camellia* seed extract or water, demonstrating that the vegetable cleansers in accordance with the present invention was effective at removing worms from harvested vegetables.

Figure 2:
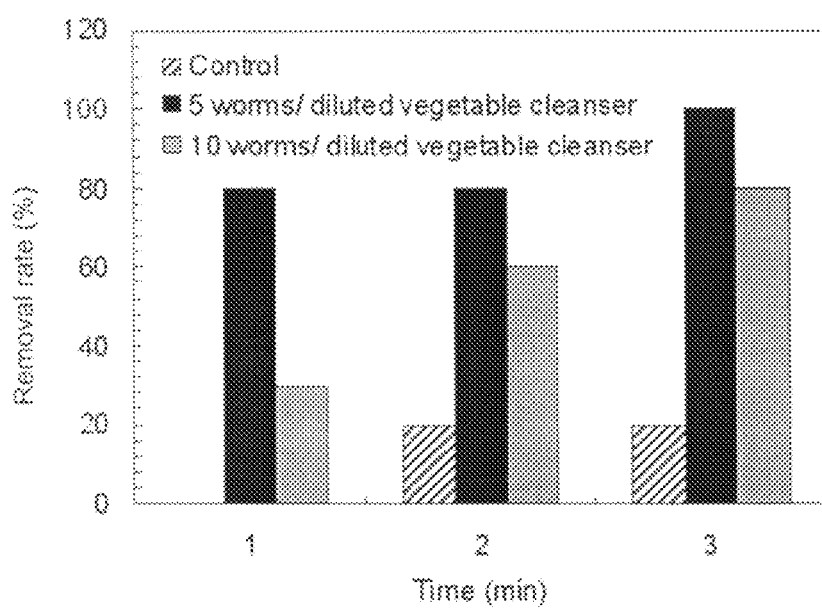
FIG. 2 illustrates removal rates of vegetable cleanser and water according to Table 3.

Numbers of worms removed by treatment of diluted vegetable cleanser and water are shown in Table 3. As shown in FIG. 2, the removal rates of vegetable cleanser being calculated according to Table 3 were from 80% to 100%, i.e. 80% to 100% worms were removed by treatment of diluted vegetable cleanser, within 3 minutes, which was three to four times more effective than control groups.

TABLE 3

Removing effect of diluted vegetable cleanser on vegetables harboring different numbers of worms

| | Treatment | | | | | | | |
|---|---|---|---|---|---|---|---|---|
| | Water | | | Diluted vegetable cleanser (1:50 dilution) | | | | |
| Time[b] | 5 worms[a] | | | 5 worms | | | 10 worms | |
| 1 minute | 0[c] | 0 | 0 | 4 | 3 | 3 | 3 | 3 | 2 |
| 2 minutes | 1 | 0 | 1 | 4 | 3 | 4 | 6 | 5 | 6 |
| 3 minutes | 1 | 0 | 1 | 5 | 4 | 5 | 8 | 7 | 8 |

[a]Number of worms harbored on each sample vegetable.
[b]Time after vegetables subject to various treatments.
[c]Number of floating or sunk worms, which was counted cumulatively and accumulated with time after vegetables were subjected to various treatments.

Furthermore, effectiveness of different means for removing worms from sample vegetables was evaluated by number of worms removed by soaking, washing and stirring in diluted vegetable cleanser. Vegetables that were cleaned by water were used as controls. The results show that the stirring method for cleaning may save time and is effective.

TABLE 4

Results of different methods of removing worms from harvested vegetables

| | Treatment* Cleanser (water) | | | |
|---|---|---|---|---|
| Time | Soak | Rinse | Stir (50 rpm) | Stir (105 rpm)[a] |
| 30 seconds[b] | — | — | — | 1 |
| 1 minute | — | — | 1 | 2 |
| 3 minutes | — | — | — | — |
| 5 minutes | — | 1 | 2 | — |
| 20 minutes | 1[c] | 2 | — | — |
| Removal rate (%)[d] | 20 | 40 | 40 | 40 |

*For each treatment, 3 individual experiments were performed. The floating or sunk worms were evaluated as being removed by the treatments. The number of floating or sunk worms was counted accumulatively with time after the vegetables were subjected various treatments.
[a]Stir bar could not work normally at a speed of 120 rpm.
[b]Time after vegetables subject to various treatments.
[c]Number of floating or sunk worms, which was counted cumulatively and accumulated with time after vegetables were subjected to various treatments.
[d]The removal rate of the vegetable cleanser to pest that was calculated as ratio of the number of floating or sunk pests to that of pests originally resided on the vegetable.

In view of the results described above, it was demonstrated that pests might be stimulated and relaxed by the vegetable cleanser in accordance with the present invention. Pests could be effectively removed by using vegetable cleanser in accordance with the present invention to reduce amounts of or

TABLE 2

Comparison of different treatment for removing pests from harvested vegetables

| | Treatment[a] | | | | | | | | | | | | | | |
|---|---|---|---|---|---|---|---|---|---|---|---|---|---|---|---|
| | Water | | | | | *Oiltea camellia* seed extract (1:200 dilution) | | | | | Diluted vegetable cleanser (1:50 dilution) | | | | |
| Time[b] | | | | | | | | | | | | | | | |
| 30" | 0[c] | 0 | 0 | 0 | 0 | 1 | 0 | 1 | 0 | 1 | 0 | 1 | 1 | 0 | 1 |
| 1'20" | 1 | 0 | 1 | 1 | 0 | 1 | 1 | 1 | 0 | 1 | 4 | 4 | 4 | 3 | 3 |
| 3'10" | 1 | 0 | 1 | 1 | 0 | 1 | 1 | 1 | 0 | 1 | 5 | 5 | 5 | 5 | 4 |

[a]For each treatment, 5 individual experiments were performed. The floating or sunk worms were evaluated as being removed by the treatments.
[b]Time after vegetables subject to various treatments.
[c]Number of floating or sunk time worms, which was counted cumulatively and accumulated with time after vegetables were subjected to various treatments.

completely clean up pests on vegetables. Further, the vegetable cleanser may include more than one kind vegetable to clean various vegetables. The present invention is useful in a vegetable-processing factory for preparing ready-to-eat food, such as salad. Vegetables are processed to remove their impalatable parts. Therefore, the impalatable parts could be collected for preparing the vegetable cleanser. Then the obtained vegetable cleanser may be filtered or diluted with water to remove pests from uncollected parts by soaking, washing or stirring the uncollected parts with the filtered or diluted vegetable cleanser. Finally, once the pests are removed from the vegetables, the cleaned vegetables could be further prepared and packed as ready-to-eat food. For sake of increasing value of agricultural products, vegetables could be subject to vegetable cleanser in accordance with the present invention to remove pests therefrom without applying chemical pesticides thereto.

Even though numerous characteristics and advantages of the present invention have been set forth in the foregoing description, together with details of the structure and features of the invention, the disclosure is illustrative only. Changes may be made in the details within the principles of the invention to the full extent indicated by the broad general meaning of the terms in which the appended claims are expressed.

What is claimed is:

1. A method for removing pests from the harvested vegetables, comprising:
    extracting a first portion of harvested vegetables with water to obtain a diluted vegetable cleanser,
    soaking, washing or stirring a second portion of the harvested vegetables in the diluted vegetable cleanser, such that pests residing on the second portion of the harvested vegetables are removed from the second portion of the harvested vegetables,
    wherein the first portion of harvested vegetables and the second portion of harvested vegetables independently contain vegetables selected from the group consisting of harvested vegetables belonging to *Brassica oleracea, Brassica oleracea* L., *Brassica oleracea* var.italica, *Brassica napus, Brassica rapa* perkinensis, *Raphanus sativus, Lactuca sativa* Linn, *Spinacia oleracea* L. and *Amaranthus tricolor* L and wherein the pests are selected from the group consisting of *Plutellidae* and *Pieridae*.

2. The method as claimed in claim 1, wherein the vegetables are selected from the group consisting of *Brassica oleracea, Brassica oleracea* var. italica and a combination thereof.

3. The method as claimed in claim 1, further comprising steps of:
    collecting impalatable parts of harvested vegetables to provide the first portion of harvested vegetables and to leave uncollected parts of the vegetables as the second portion of harvested vegetables.

4. The method as claimed in claim 3, wherein the impalatable parts are selected from the group consisting of roots, stems, leaves, flowers, fruits and a combination thereof.

5. The method as claimed in claim 3, wherein the impalatable parts are selected from the group consisting of old leaves, damaged leaves and a combination thereof.

6. The method as claimed in claim 1, further comprising steps of:
    filtering the vegetable cleanser to obtain a filtered vegetable cleanser and cleaning the second portion of harvested vegetables with the filtered vegetable cleanser.

7. The method as claimed in claim 6, further comprising steps of:
    diluting the filtered vegetable cleanser to obtain a diluted vegetable cleanser and cleaning the second portion of harvested vegetables with the diluted vegetable cleanser.

8. The method as claimed in claim 7, wherein diluting of the filtered vegetable cleanser comprises diluting filtered vegetable cleanser with water at about a ratio of 1:50 by volume.

9. The method as claimed in claim 6, wherein the step of cleaning the second portion of harvested vegetables comprises stirring the second portion of harvested vegetables in the vegetable cleanser at a stirring rate ranging from about 50 to 110 rpm.

10. The method as claimed in claim p claim 1, wherein the pests are selected from the group consisting of *Plutella* and *Pieris*.

11. The method as claimed in claim 1, wherein the pests are *Plutella xylostella* or *Pieris rapae* crucivora Boisduval.

12. A method for removing pests from a vegetable, comprising:
    washing a first vegetable with a cleanser extracted from a second vegetable,
    wherein the first vegetable and the second vegetable are selected from the group consisting of vegetables belonging to *Brassica oleracea, Brassica oleracea* L., *Brassica oleracea* var.italica, *Brassica napus, Brassica rapa* perkinensis, *Raphanus sativus, Lactuca sativa* Linn, *Spinacia oleracea* L. and *Amaranthus tricolor* L, and wherein the pests are selected from the group consisting of *Plutellidae* and *Pieridae*.

13. The method as claimed in claim 12, wherein the first vegetable and the second vegetable are the same vegetable.

14. The method as claimed in claim 13, wherein the second vegetable is an impalatable part of the first vegetable.

15. The method as claimed in claim 12, wherein the first vegetable and the second vegetable are different vegetables.

16. The method as claimed in claim 12, wherein the cleanser is extracted by homogenizing the second vegetable and filtering the homogenate to remove debris.

* * * * *